(12) United States Patent
Lee (10) Patent No.: US 9,273,138 B2
(45) Date of Patent: Mar. 1, 2016

(54) HUMANIZED FORMS OF MONOCLONAL ANTIBODIES TO HUMAN GNRH RECEPTOR

(71) Applicant: Vancouver Biotech LTD., Vancouver (CA)

(72) Inventor: Gregory Lee, Vancouver (CA)

(73) Assignee: VANCOUVER BIOTECH LTD., Vancouver (CA)

( * ) Notice: Subject to any disclaimer, the term of this patent is extended or adjusted under 35 U.S.C. 154(b) by 0 days.

(21) Appl. No.: 13/797,653

(22) Filed: Mar. 12, 2013

(65) Prior Publication Data

US 2014/0030253 A1 Jan. 30, 2014

Related U.S. Application Data

(60) Provisional application No. 61/676,763, filed on Jul. 27, 2012.

(51) Int. Cl.
| | |
|---|---|
| *C07K 16/28* | (2006.01) |
| *A61K 39/395* | (2006.01) |
| *A61K 45/06* | (2006.01) |
| *G01N 33/74* | (2006.01) |

(52) U.S. Cl.
CPC ......... *C07K 16/2869* (2013.01); *A61K 39/3955* (2013.01); *A61K 45/06* (2013.01); *G01N 33/74* (2013.01); *C07K 2317/24* (2013.01); *G01N 2800/7023* (2013.01)

(58) Field of Classification Search
None
See application file for complete search history.

(56) References Cited

U.S. PATENT DOCUMENTS

| | | |
|---|---|---|
| 8,163,283 B2 | 4/2012 | Lee |
| 8,361,793 B2 | 1/2013 | Lee |

FOREIGN PATENT DOCUMENTS

WO   WO-2011/026242   3/2011

OTHER PUBLICATIONS

International Search Report and Written Opinion for PCT/IB2013/002174, mailed Jan. 24, 2014, 11 pages.
Lee et al., "Growth inhibition of tumor cells in vitro by using monoclonal antibodies against gonadotropin-releasing hormone receptor," Cancer Immunol Immunother (2010) 59:1011-1019.
Lee et al., "CA215 and GnRH receptor as targets for cancer therapy," Cancer Immunol Immunother (2012) 61:1805-1817.

*Primary Examiner* — Michael Pak
(74) *Attorney, Agent, or Firm* — Morrison & Foerster LLP (57) ABSTRACT

Humanized forms of murine GHR106 monoclonal antibodies and methods of using them are described. Humanized GHR106 monoclonal antibodies have high affinity and specificity to the corresponding tumor-associated antigen, gonadotropin-releasing hormone (GnRH) receptor comparable to murine GHR106.

15 Claims, 6 Drawing Sheets

1 H40 L42
2 H64 L42
3 H65 L42
4 H66 L42
5 Negative control

Reducing conditions

Heavy chain

```
                    FR1                      CDR1    FR2                CDR2
hGHR106_H65  QVQLQESGPGLVKPSETLSLVCTVSGFSLS  RYSVH  WIRQPPGKGLEWIG  MIWGG-STDYN  59
hGHR106_H66  QVQLKESGPGLVKPSETLSLVCTVSGFSLS  RYSVH  WIRQPPGKGLEWIG  MIWGGGSTDYN  60
hGHR106_H64  QVQLQESGPGLVKPSETLSLTCTVSGFSLS  RYSVH  WIRQPPGKGLEWIG  MIWGGGSTDYN  60
GHR106_Murine QVQLKESGPGLVAPSQSLSITCTVSGFSLS  RYSVH  WVRQPPGKGLEWLG  MIWGGGSTDYN  60
             ****:******* **::**:.********* *****  *:**********:*  ***** *****

FR3                      CDR3          FR4
hGHR106_H65  SSLQS RVTISKDNSKSQVFLKMSSVTAADTAMYYCAR  GNDGYYSFAY  WGQGTLVTVSS  117
hGHR106_H66  SSLQS RVTISKDNSKSQVFLKMSSVTAADTAMYYCAR  GNDGYYSFAY  WGQGTLVTVSS  118
hGHR106_H64  PSLKS RVTISKDNSKSQVFLKMSSVTAADTAMYYCAR  GNDGYYSFAY  WGQGTLVTVSS  118
GHR106_Murine SALKS RLSISKDNSKSQVFLKMNSLQTDDTAMYYCAR  GNDGYYSFAY  WGQGTLVTVSS  118
             .:*:*  *::**************.*: :  **********  **********  ***********
```

Light chain

```
                    FR1                   CDR1            FR2             CDR2
hGHR106_L41  DIVMTQSPDSLAVSLGERATINC  KSSQSLLNSRTRKNYLA  WYQQKPGQPPKLLIY  WASTR  60
hGHR106_L42  DIVMTQSPDSLAVSLGERATINC  KSSQSLLNSRTRKNYLA  WYQQKPGQSPKLLIY  WASTR  60
hGHR106_L43  DIVMTQSPDSLAVSLGERATINC  KSSQSLLNSRTRKNYLA  WYQQKPGQPPKLLIY  WASTR  60
GHR106_Murine DIVMSQSPSSLAVSAGEKVTMSC  KSSQSLLNSRTRKNYLA  WYQQKPGQSPKLLIY  WASTR  60
             ****:***.***** **:.*:.*  *****************  ********.******  *****

FR3                          CDR3       FR4
hGHR106_L41  ES GVPDRFSGSGSGTDFTLTISSLQAEDVAVYYC  KQSYNLYT  FGQGTKLEIK  112
hGHR106_L42  ES GVPDRFSGSGSGTDFTLTISSLQAEDVAVYYC  KQSYNLYT  FGQGTKLEIK  112
hGHR106_L43  ES GVPDRFSGSGSGTDFTLTISSLQAEDVAVYYC  KQSYNLYT  FGGGTKLEIK  112
GHR106_Murine ES GVPDRFTGSGSGTDFTLTISVQAEDLAVYYC  KQSYNLYT  FGGGTKLEIK  112
             ** *******:***********.****:*****  ********  *******
```

Figure 6

Heavy Chains p7164 (hGHR106_H64)
ATGGAGACCGACACCCTGCTGCTCTGGGTGCTGCTGCTCTGGGTGCCCGGCTCCACCGGACAGGTT
CAGTTGCAAGAGTCTGGTCCCGGCCTGGTTAAACCCTCTGAGACTTTGAGCTTGACATGCACCGTA
AGCGGCTTCTCTCTGAGCCGGTACTCTGTACACTGGATTCGACAGCCTCCTGGCAAGGGCCTGGAA
TGGATTGGCATGATCTGGGGCGGCGGAAGTACAGATTATAACCCTTCCTTGAAGAGCCGCGTCACC
ATCTCTAAGGACAACAGCAAGTCCCAGGTCTTCCTGAAGATGTCAAGCGTCACCGCTGCCGACACC
GCCATGTACTACTGTGCACGGGGGAATGACGGATACTACAGTTTCGCATATTGGGGCCAGGGAACA
CTGGTTACAGTGTCTAGTGCTAGCACCAAGGGCCCCAGCGTGTTCCCTCTGGCCCCAGCAGCAAG
AGCACCAGCGGCGGAACCGCCGCCCTGGGCTGCCTGGTGAAGGACTACTTCCCCGAGCCCGTGACC
GTGTCCTGGAACAGCGGCGCTCTGACCAGCGGAGTGCACACCTTCCCTGCCGTGCTGCAGAGCAGC
GGCCTGTACTCCCTGAGCAGCGTGGTGACCGTGCCCAGCAGCAGCCTGGGCACCCAGACCTACATC
TGCAACGTGAACCACAAGCCCTCCAACACCAAGGTGGACAAGAAGGTGGAGCCTAAGAGCTGCGAC
AAGACCCACACCTGCCCTCCCTGCCCCGCCCCCGAGCTGCTGGGCGGACCCAGCGTGTTCCTGTTC
CCTCCCAAGCCCAAGGACACCCTGATGATCAGCCGGACCCCCGAGGTGACCTGCGTGGTGGTGGAC
GTGAGCCACGAGGACCCCGAGGTGAAGTTCAACTGGTACGTGGACGGCGTGGAGGTGCACAACGCC
AAGACCAAGCCTCGGGAGGAGCAGTACAACTCCACCTACCGCGTGGTGAGCGTGCTGACCGTGCTG
CACCAGGACTGGCTGAACGGCAAGGAGTACAAGTGCAAGGTGAGCAACAAGGCCCTGCCCGCTCCC
ATCGAGAAGACCATCAGCAAGGCCAAGGGCCAGCCCCGGGAGCCTCAGGTGTACACCCTGCCCCCC
AGCCGCGACGAGCTGACCAAGAACCAGGTGAGCCTGACCTGCCTGGTGAAGGGCTTCTACCCCTCC
GACATCGCCGTGGAGTGGGAGAGCAACGGCCAGCCTGAGAACAACTACAAGACCACCCCTCCCGTG
CTGGACAGCGACGGCAGCTTCTTCCTGTACAGCAAGCTGACCGTGGACAAGTCCCGGTGGCAGCAG
GGCAACGTGTTCAGCTGCAGCGTGATGCACGAGGCCCTGCACAACCACTACACCCAGAAGAGCCTG
AGCCTGAGCCCCGGAAAGTAA p7165 (hGHR106_H65)
ATGGAGACCGACACCCTGCTGCTCTGGGTGCTGCTGCTCTGGGTGCCCGGCTCCACCGGACAGGTT
CAGTTGCAAGAGTCTGGTCCCGGCCTGGTTAAACCCTCTGAGACTTTGAGCTTGGTCTGCACCGTA
AGCGGCTTCTCTCTGAGCCGGTACTCTGTACACTGGATTCGACAGCCTCCTGGCAAGGGCCTGGAA
TGGATTGGCATGATCTGGGGCGGCGGAAGTACAGATTATAACAGCTCCTTGCAGAGCCGCGTCACC
ATCTCTAAGGACAACAGCAAGTCCCAGGTCTTCCTGAAGATGTCAAGCGTCACCGCTGCCGACACC
GCCATGTACTACTGTGCACGGGGGAATGACGGATACTACAGTTTCGCATATTGGGGCCAGGGAACA
CTGGTTACAGTGTCTAGTGCTAGCACCAAGGGCCCCAGCGTGTTCCCTCTGGCCCCAGCAGCAAG
AGCACCAGCGGCGGAACCGCCGCCCTGGGCTGCCTGGTGAAGGACTACTTCCCCGAGCCCGTGACC
GTGTCCTGGAACAGCGGCGCTCTGACCAGCGGAGTGCACACCTTCCCTGCCGTGCTGCAGAGCAGC
GGCCTGTACTCCCTGAGCAGCGTGGTGACCGTGCCCAGCAGCAGCCTGGGCACCCAGACCTACATC
TGCAACGTGAACCACAAGCCCTCCAACACCAAGGTGGACAAGAAGGTGGAGCCTAAGAGCTGCGAC
AAGACCCACACCTGCCCTCCCTGCCCCGCCCCCGAGCTGCTGGGCGGACCCAGCGTGTTCCTGTTC
CCTCCCAAGCCCAAGGACACCCTGATGATCAGCCGGACCCCCGAGGTGACCTGCGTGGTGGTGGAC
GTGAGCCACGAGGACCCCGAGGTGAAGTTCAACTGGTACGTGGACGGCGTGGAGGTGCACAACGCC
AAGACCAAGCCTCGGGAGGAGCAGTACAACTCCACCTACCGCGTGGTGAGCGTGCTGACCGTGCTG
CACCAGGACTGGCTGAACGGCAAGGAGTACAAGTGCAAGGTGAGCAACAAGGCCCTGCCCGCTCCC
ATCGAGAAGACCATCAGCAAGGCCAAGGGCCAGCCCCGGGAGCCTCAGGTGTACACCCTGCCCCCC
AGCCGCGACGAGCTGACCAAGAACCAGGTGAGCCTGACCTGCCTGGTGAAGGGCTTCTACCCCTCC
GACATCGCCGTGGAGTGGGAGAGCAACGGCCAGCCTGAGAACAACTACAAGACCACCCCTCCCGTG
CTGGACAGCGACGGCAGCTTCTTCCTGTACAGCAAGCTGACCGTGGACAAGTCCCGGTGGCAGCAG
GGCAACGTGTTCAGCTGCAGCGTGATGCACGAGGCCCTGCACAACCACTACACCCAGAAGAGCCTG
AGCCTGAGCCCCGGAAAGTAA

FIG.7A p7166 (hGHR106_H66)
ATGGAGACCGACACCCTGCTGCTCTGGGTGCTGCTGCTCTGGGTGCCCGGCTCCACCGGACAGGTT
CAGTTGAAGGAGTCTGGTCCCGGCCTGGTTAAACCCTCTGAGACTTTGAGCTTGGTCTGCACCGTA
AGCGGCTTCTCTCTGAGCCGGTACTCTGTACACTGGATTCGACAGCCTCCTGGCAAGGGCCTGGAA
TGGATTGGCATGATCTGGGGCGGCGGAAGTACAGATTATAACAGCTCCTTGCAGAGCCGCGTCACC
ATCTCTAAGGACAACAGCAAGTCCCAGGTCTTCCTGAAGATGTCAAGCGTCACCGCTGCCGACACC
GCCATGTACTACTGTGCACGGGGGAATGACGGATACTACAGTTTCGCATATTGGGGCCAGGGAACA
CTGGTTACAGTGTCTAGTGCTAGCACCAAGGGCCCCAGCGTGTTCCCTCTGGCCCCCAGCAGCAAG
AGCACCAGCGGCGGAACCGCCGCCCTGGGCTGCCTGGTGAAGGACTACTTCCCCGAGCCCGTGACC
GTGTCCTGGAACAGCGGCGCTCTGACCAGCGGAGTGCACACCTTCCCTGCCGTGCTGCAGAGCAGC
GGCCTGTACTCCCTGAGCAGCGTGGTGACCGTGCCCAGCAGCAGCCTGGGCACCCAGACCTACATC
TGCAACGTGAACCACAAGCCCTCCAACACCAAGGTGGACAAGAAGGTGGAGCCTAAGAGCTGCGAC
AAGACCCACACCTGCCCTCCCTGCCCCGCCCCCGAGCTGCTGGGCGGACCCAGCGTGTTCCTGTTC
CCTCCCAAGCCCAAGGACACCCTGATGATCAGCCGCACCCCCGAGGTGACCTGCGTGGTGGTGGAC
GTGAGCCACGAGGACCCCGAGGTGAAGTTCAACTGGTACGTGGACGGCGTGGAGGTGCACAACGCC
AAGACCAAGCCTCGGGAGGAGCAGTACAACTCCACCTACCGCGTGGTGAGCGTGCTGACCGTGCTG
CACCAGGACTGGCTGAACGGCAAGGAGTACAAGTGCAAGGTGAGCAACAAGGCCCTGCCCGCTCCC
ATCGAGAAGACCATCAGCAAGGCCAAGGGCCAGCCCCGGGAGCCTCAGGTGTACACCCTGCCCCCC
AGCCGCGACGAGCTGACCAAGAACCAGGTGAGCCTGACCTGCCTGGTGAAGGGCTTCTACCCCTCC
GACATCGCCGTGGAGTGGGAGAGCAACGGCCAGCCTGAGAACAACTACAAGACCACCCCTCCCGTG
CTGGACAGCGACGGCAGCTTCTTCCTGTACAGCAAGCTGACCGTGGACAAGTCCCGGTGGCAGCAG
GGCAACGTGTTCAGCTGCAGCGTGATGCACGAGGCCCTGCACAACCACTACACCCAGAAGAGCCTG
AGCCTGAGCCCCGGAAAGTAA

Light Chains pCD3_L0041 (hGHR106_L41)
ATGGAGACCGACACCCTGCTGCTCTGGGTGCTGCTGCTCTGGGTGCCCGGCTCCACCGGAGATATC
GTAATGACTCAGTCCCCCGATAGCCTCGCTGTGTCATTGGGTGAACGGGCAACTATTAACTGTAAG
TCATCACAAAGCCTCCTTAATTCTAGGACCAGGAAAAACTACCTGGCATGGTATCAACAGAAGCCA
GGACAGCCACCAAAGCTGCTGATCTACTGGGCTTCTACAAGAGAGAGTGGAGTGCCAGACCGCTTC
TCCGGCTCCGGGAGCGGCACTGATTTACCCTCACTATCAGCTCCCTTCAGGCACAGGATGTGGCC
GTGTACTATTGCAAGCAGAGCTACAACCTCTACACCTTCGGCCAGGGGACTAAACTGGAAATTAAG
CGGACCGTGGCCGCCCCAGCGTGTTCATCTTCCCTCCCAGCGACGAGCAGCTGAAGTCTGGCACC
GCCAGCGTGGTGTGCCTGCTGAACAACTTCTACCCCGCGAGGCCAAGGTGCAGTGGAAGGTGGAC
AACGCCCTGCAGAGCGGCAACAGCCAGGAGAGCGTGACCGAGCAGGACTCCAAGGACAGCACCTAC
AGCCTGAGCAGCACCCTGACCCTGAGCAAGGCCGACTACGAGAAGCACAAGGTGTACGCCTGCGAG
GTGACCCACCAGGGACTGTCTAGCCCCGTGACCAAGAGCTTCAACCGGGGCGAGTGCTAA pCD3_L0042 (hGHR106_L42)
ATGGAGACCGACACCCTGCTGCTCTGGGTGCTGCTGCTCTGGGTGCCCGGCTCCACCGGAGATATC
GTAATGACTCAGTCCCCCGATAGCCTCGCTGTGTCATTGGGTGAACGGGCAACTATTAACTGTAAG
TCATCACAAAGCCTCCTTAATTCTAGGACCAGGAAAAACTACCTGGCATGGTATCAACAGAAGCCA
GGACAGTCACCAAAGCTGCTGATCTACTGGGCTTCTACAAGAGAGAGTGGAGTGCCAGACCGCTTC
TCCGGCTCCGGGAGCGGCACTGATTTACCCTCACTATCAGCTCCCTTCAGGCAGAGGATGTGGCC
GTGTACTATTGCAAGCAGAGCTACAACCTCTACACCTTCGGCCAGGGGACTAAACTGGAAATTAAG
CGGACCGTGGCCGCCCCAGCGTGTTCATCTTCCCTCCCAGCGACGAGCAGCTGAAGTCTGGCACC
GCCAGCGTGGTGTGCCTGCTGAACAACTTCTACCCCGCGAGGCCAAGGTGCAGTGGAAGGTGGAC
AACGCCCTGCAGAGCGGCAACAGCCAGGAGAGCGTGACCGAGCAGGACTCCAAGGACAGCACCTAC
AGCCTGAGCAGCACCCTGACCCTGAGCAAGGCCGACTACGAGAAGCACAAGGTGTACGCCTGCGAG
GTGACCCACCAGGGACTGTCTAGCCCCGTGACCAAGAGCTTCAACCGGGGCGAGTGCTAA

FIG.7B pCD3_L0043 (hGHR106_L43)
ATGGAGACCGACACCCTGCTGCTCTGGGTGCTGCTGCTCTGGGTGCCCGGCTCCACCGGAGATATC
GTAATGACTCAGTCCCCCGATAGCCTCGCTGTGTCATTGGGTGAACGGGCAACTATTAACTGTAAG
TCATCACAAAGCCTCCTTAATTCTAGGACCAGGAAAAACTACCTGGCATGGTATCAACAGAAGCCA
GGACAGCCACCAAAGCTGCTGATCTACTGGGCTTCTACAAGAGAGAGTGGAGTGCCAGACCGCTTC
TCCGGCTCCGGGAGCGGCACTGATTTTACCCTCACTATCAGCTCCCTTCAGGCAGAGGATGTGGCC
GTGTACTATTGCAAGCAGAGCTACAACCTCTACACCTTCGGCGGAGGGACTAAACTGGAAATTAAG
CGGACCGTGGCCGCCCCAGCGTGTTCATCTTCCCTCCCAGCGACGAGCAGCTGAAGTCTGGCACC
GCCAGCGTGGTGTGCCTGCTGAACAACTTCTACCCCGCGAGGCCAAGGTGCAGTGGAAGGTGGAC
AACGCCCTGCAGAGCGGCAACAGCCAGGAGAGCGTGACCGAGCAGGACTCCAAGGACAGCACCTAC
AGCCTGAGCAGCACCCTGACCCTGAGCAAGGCCGACTACGAGAAGCACAAGGTGTACGCCTGCGAG
GTGACCCACCAGGGACTGTCTAGCCCCGTGACCAAGAGCTTCAACCGGGGCGAGTGCTAA

FIG.7C

SEQUENCE LISTING

```
<160> NUMBER OF SEQ ID NOS: 22

<210> SEQ ID NO 1
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(5)
<223> OTHER INFORMATION: CDR1 region of heavy chain of hGHR106

<400> SEQUENCE: 1

Arg Tyr Ser Val His
1               5

<210> SEQ ID NO 2
<211> LENGTH: 17
<212> TYPE: PRT
<213> ORGANISM: Artificial Sequence
```

```
<220> FEATURE:
<223> OTHER INFORMATION: synthetic construct
<220> FEATURE:
<221> NAME/KEY: CHAIN
<222> LOCATION: (1)...(17)
<223> OTHER INFORMATION: CDR2 region of heavy chain of hGHR106

<400> SEQUENCE: 2

Met Ile Trp Gly Gly Gly Ser Thr Asp Tyr Asn Ser Pro Ser Leu Lys
 1               5                  10                  15

Ser

<210> SEQ ID NO 3
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(16)
<223> OTHER INFORMATION: CDR2 region of heavy chain of hGHR106

<400> SEQUENCE: 3

Met Ile Trp Gly Gly Gly Ser Thr Asp Tyr Asn Ser Ser Leu Gln Ser
 1               5                  10                  15

<210> SEQ ID NO 4
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(15)
<223> OTHER INFORMATION: CDR2 region of heavy chain of hGHR106

<400> SEQUENCE: 4

Met Ile Trp Gly Gly Ser Thr Asp Tyr Asn Ser Ser Leu Gln Ser
 1               5                  10                  15

<210> SEQ ID NO 5
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(10)
<223> OTHER INFORMATION: CDR3 region of heavy chain of hGHR106

<400> SEQUENCE: 5

Gly Asn Asp Gly Tyr Tyr Ser Phe Ala Tyr
 1               5                  10

<210> SEQ ID NO 6
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(17)
<223> OTHER INFORMATION: CDR1 region of light chain of hGHR106
```

-continued

```
<400> SEQUENCE: 6

Lys Ser Ser Gln Ser Leu Leu Asn Ser Arg Thr Arg Lys Asn Tyr Leu
1               5                   10                  15

Ala

<210> SEQ ID NO 7
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(7)
<223> OTHER INFORMATION: CDR2 region of light chain of hGHR106

<400> SEQUENCE: 7

Trp Ala Ser Thr Arg Glu Ser
1               5

<210> SEQ ID NO 8
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(80)
<223> OTHER INFORMATION: CDR3 region of light chain of hGHR106

<400> SEQUENCE: 8

Lys Gln Ser Tyr Asn Leu Tyr Thr
1               5

<210> SEQ ID NO 9
<211> LENGTH: 117
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(117)
<223> OTHER INFORMATION: heavy chain of hGHR106_H65

<400> SEQUENCE: 9

Gln Val Gln Leu Gln Glu Ser Gly Pro Gly Leu Val Lys Pro Ser Glu
1               5                   10                  15

Thr Leu Ser Leu Val Cys Thr Val Ser Gly Phe Ser Leu Ser Arg Tyr
                20                  25                  30

Ser Val His Trp Ile Arg Gln Pro Pro Gly Lys Gly Leu Glu Trp Ile
            35                  40                  45

Gly Met Ile Trp Gly Gly Ser Thr Asp Tyr Asn Ser Ser Leu Gln Ser
        50                  55                  60

Arg Val Thr Ile Ser Lys Asp Asn Ser Lys Ser Gln Val Phe Leu Lys
65                  70                  75                  80

Met Ser Ser Val Thr Ala Ala Asp Thr Ala Met Tyr Tyr Cys Ala Arg
                85                  90                  95

Gly Asn Asp Gly Tyr Tyr Ser Phe Ala Tyr Trp Gly Gln Gly Thr Leu
                100                 105                 110

Val Thr Val Ser Ser
            115
```

<210> SEQ ID NO 10
<211> LENGTH: 118
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(118)
<223> OTHER INFORMATION: heavy chain of hGHR106_H66

<400> SEQUENCE: 10

```
Gln Val Gln Leu Lys Glu Ser Gly Pro Gly Leu Val Lys Pro Ser Glu
 1               5                  10                  15

Thr Leu Ser Leu Val Cys Thr Val Ser Gly Phe Ser Leu Ser Arg Tyr
            20                  25                  30

Ser Val His Trp Ile Arg Gln Pro Pro Gly Lys Gly Leu Glu Trp Ile
        35                  40                  45

Gly Met Ile Trp Gly Gly Ser Thr Asp Tyr Asn Ser Ser Leu Gln
    50                  55                  60

Ser Arg Val Thr Ile Ser Lys Asp Asn Ser Lys Ser Gln Val Phe Leu
65                  70                  75                  80

Lys Met Ser Ser Val Thr Ala Ala Asp Thr Ala Met Tyr Tyr Cys Ala
                85                  90                  95

Arg Gly Asn Asp Gly Tyr Tyr Ser Phe Ala Tyr Trp Gly Gln Gly Thr
            100                 105                 110

Leu Val Thr Val Ser Ser
        115
```

<210> SEQ ID NO 11
<211> LENGTH: 118
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(118)
<223> OTHER INFORMATION: heavy chain of hGHR106_H64

<400> SEQUENCE: 11

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ser Arg Tyr
            20                  25                  30

Ser Val His Trp Ile Arg Gln Pro Pro Gly Lys Gly Leu Glu Trp Ile
        35                  40                  45

Gly Met Ile Trp Gly Gly Ser Thr Asp Tyr Asn Pro Ser Leu Lys
    50                  55                  60

Ser Arg Val Thr Ile Ser Lys Asp Asn Ser Lys Ser Gln Val Phe Leu
65                  70                  75                  80

Lys Met Ser Ser Val Thr Ala Ala Asp Thr Ala Met Tyr Tyr Cys Ala
                85                  90                  95

Arg Gly Asn Asp Gly Tyr Tyr Ser Phe Ala Tyr Trp Gly Gln Gly Thr
            100                 105                 110

Leu Val Thr Val Ser Ser
        115
```

<210> SEQ ID NO 12
<211> LENGTH: 118
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(118)
<223> OTHER INFORMATION: heavy chain of hGHR106_Murine

<400> SEQUENCE: 12

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
            20                  25                  30

Ser Val His Trp Val Arg Gln Pro Pro Gly Lys Gly Leu Glu Trp Leu
        35                  40                  45

Gly Met Ile Trp Gly Gly Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Gly Asn Asp Gly Tyr Tyr Ser Phe Ala Tyr Trp Gly Gln Gly Thr
            100                 105                 110

Leu Val Thr Val Ser Ser
        115

<210> SEQ ID NO 13
<211> LENGTH: 112
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(112)
<223> OTHER INFORMATION: light chain of hGHR106_L41

<400> SEQUENCE: 13

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Tyr Thr Phe Gly Gln Gly Thr Lys Leu Glu Ile Lys
            100                 105                 110

<210> SEQ ID NO 14
<211> LENGTH: 112
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(112)
<223> OTHER INFORMATION: light chain of hGHR106_L42

<400> SEQUENCE: 14

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Tyr Thr Phe Gly Gln Gly Thr Lys Leu Glu Ile Lys
            100                 105                 110

<210> SEQ ID NO 15
<211> LENGTH: 112
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(112)
<223> OTHER INFORMATION: light chain of hGHR106_L43

<400> SEQUENCE: 15

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Tyr Thr Phe Gly Gly Gly Thr Lys Leu Glu Ile Lys
            100                 105                 110

<210> SEQ ID NO 16
<211> LENGTH: 112
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(112)
<223> OTHER INFORMATION: light chain of hGHR106_Murine

```
<400> SEQUENCE: 16

Asp Ile Val Met Ser Gln Ser Pro Ser Ser Leu Ala Val Ser Ala Gly
 1               5                  10                  15

Glu Lys Val Thr Met Ser Cys Lys Ser Ser Gln Ser Leu Leu Asn Ser
             20                  25                  30

Arg Thr Arg Lys Asn Tyr Leu Ala Trp Tyr Gln Gln Lys Pro Gly Gln
         35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                 85                  90                  95

Ser Tyr Asn Leu Tyr Thr Phe Gly Gly Gly Thr Lys Leu Glu Ile Lys
                100                 105                 110

<210> SEQ ID NO 17
<211> LENGTH: 1407
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(1407)
<223> OTHER INFORMATION: p7164 encoding hGHR106_H64

<400> SEQUENCE: 17
```

| | |
|---|---|
| atggagaccg acaccctgct gctctgggtg ctgctgctct gggtgcccgg ctccaccgga | 60 |
| caggttcagt tgcaagagtc tggtcccggc ctggttaaac cctctgagac tttgagcttg | 120 |
| acatgcaccg taagcggctt ctctctgagc cggtactctg tacactggat tcgacagcct | 180 |
| cctggcaagg gcctggaatg gattggcatg atctggggcg gcggaagtac agattataac | 240 |
| ccttccttga agagccgcgt caccatctct aaggacaaca gcaagtccca ggtcttcctg | 300 |
| aagatgtcaa gcgtcaccgc tgccgacacc gccatgtact actgtgcacg ggggaatgac | 360 |
| ggatactaca gtttcgcata ttggggccag ggaacactgg ttacagtgtc tagtgctagc | 420 |
| accaagggcc ccagcgtgtt ccctctggcc ccagcagca gagcaccag cggcggaacc | 480 |
| gccgccctgg gctgcctggt gaaggactac ttccccgagc ccgtgaccgt gtcctggaac | 540 |
| agcggcgctc tgaccagcgg agtgcacacc ttccctgccg tgctgcagag cagcggcctg | 600 |
| tactccctga gcagcgtggt gaccgtgccc agcagcagcc tgggcaccca gacctacatc | 660 |
| tgcaacgtga accacaagcc ctccaacacc aaggtggaca gaaaggtgga gcctaagagc | 720 |
| tgcgacaaga cccacacctg ccctccctgc cccgcccccg agctgctggg cggacccagc | 780 |
| gtgttcctgt tccctcccaa gcccaaggac accctgatga tcagccgcac ccccgaggtg | 840 |
| acctgcgtgg tggtggacgt gagccacgag gaccccgagg tgaagttcaa ctggtacgtg | 900 |
| gacggcgtgg aggtgcacaa cgccaagacc aagcctcggg aggagcagta caactccacc | 960 |
| taccgcgtgg tgagcgtgct gaccgtgctg caccaggact ggctgaacgg caaggagtac | 1020 |
| aagtgcaagg tgagcaacaa ggccctgccc gctcccatcg agaagaccat cagcaaggcc | 1080 |
| aagggccagc cccgggagcc tcaggtgtac accctgcccc cagccgcga cgagctgacc | 1140 |
| aagaaccagg tgagcctgac ctgcctggtg aagggcttct accctcccga catcgccgtg | 1200 |
| gagtgggaga gcaacggcca gcctgagaac aactacaaga ccaccccctcc cgtgctggac | 1260 |

```
agcgacggca gcttcttcct gtacagcaag ctgaccgtgg acaagtcccg gtggcagcag    1320
ggcaacgtgt tcagctgcag cgtgatgcac gaggccctgc acaaccacta cacccagaag    1380
agcctgagcc tgagccccgg aaagtaa                                        1407

<210> SEQ ID NO 18
<211> LENGTH: 1407
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(1407)
<223> OTHER INFORMATION: p7165 encoding hGHR106_H65

<400> SEQUENCE: 18
atggagaccg acaccctgct gctctgggtg ctgctgctct gggtgcccgg ctccaccgga      60
caggttcagt tgcaagagtc tggtcccggc ctggttaaac cctctgagac tttgagcttg     120
gtctgcaccg taagcggctt ctctctgagc cggtactctg tacactggat tcgacagcct     180
cctggcaagg gcctggaatg gattggcatg atctggggcg gcggaagtac agattataac     240
agctccttgc agagccgcgt caccatctct aaggacaaca gcaagtccca ggtcttcctg     300
aagatgtcaa gcgtcaccgc tgccgacacc gccatgtact actgtgcacg ggggaatgac     360
ggatactaca gtttcgcata ttggggccag ggaacactgg ttacagtgtc tagtgctagc     420
accaagggcc ccagcgtgtt ccctctggcc ccagcagca agagcaccag cggcggaacc     480
gccgccctgg gctgcctggt gaaggactac ttccccgagc ccgtgaccgt gtcctggaac     540
agcggcgctc tgaccagcgg agtgcacacc ttccctgccg tgctgcagag cagcggcctg     600
tactccctga gcagcgtggt gaccgtgccc agcagcagcc tgggcaccca gacctacatc     660
tgcaacgtga accacaagcc ctccaacacc aaggtggaca gaaggtgga gcctaagagc     720 tgcgacaaga cccacacctg ccctccctgc cccgccccg agctgctggg cggacccagc     780
gtgttcctgt tccctcccaa gcccaaggac accctgatga tcagccgcac ccccgaggtg     840
acctgcgtgg tggtggacgt gagccacgag gaccccgagg tgaagttcaa ctggtacgtg     900
gacggcgtgg aggtgcacaa cgccaagacc aagcctcggg aggagcagta caactccacc     960
taccgcgtgt gagcgtgct gaccgtgctg caccaggact ggctgaacgg caaggagtac    1020
aagtgcaagg tgagcaacaa ggccctgccc gctcccatcg agaagaccat cagcaaggcc    1080
aagggccagc cccgggagcc tcaggtgtac accctgcccc cagccgcga cgagctgacc    1140 aagaaccagg tgagcctgac ctgcctggtg aagggcttct acccctccga catcgccgtg    1200
gagtgggaga gcaacggcca gcctgagaac aactacaaga ccacccctcc cgtgctggac    1260
agcgacggca gcttcttcct gtacagcaag ctgaccgtgg acaagtcccg gtggcagcag    1320
ggcaacgtgt tcagctgcag cgtgatgcac gaggccctgc acaaccacta cacccagaag    1380
agcctgagcc tgagccccgg aaagtaa                                        1407

<210> SEQ ID NO 19
<211> LENGTH: 1407
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(1407)
<223> OTHER INFORMATION: p7166 encoding hGHR106_H66
```

<400> SEQUENCE: 19

```
atggagaccg acaccctgct gctctgggtg ctgctgctct gggtgcccgg ctccaccgga    60
caggttcagt tgaaggagtc tggtcccggc ctggttaaac cctctgagac tttgagcttg   120
gtctgcaccg taagcggctt ctctctgagc cggtactctg tacactggat tcgacagcct   180
cctggcaagg gcctggaatg gattggcatg atctggggcg gcggaagtac agattataac   240
agctccttgc agagccgcgt caccatctct aaggacaaca gcaagtccca ggtcttcctg   300
aagatgtcaa gcgtcaccgc tgccgacacc gccatgtact actgtgcacg ggggaatgac   360
ggatactaca gtttcgcata ttggggccag ggaacactgg ttacagtgtc tagtgctagc   420
accaagggcc ccagcgtgtt ccctctggcc cccagcagca gagcaccagc ggcggaacc    480
gccgccctgg gctgcctggt gaaggactac ttccccgagc ccgtgaccgt gtcctggaac   540
agcggcgctc tgaccagcgg agtgcacacc ttccctgccg tgctgcagag cagcggcctg   600
tactccctga gcagcgtggt gaccgtgccc agcagcagcc tgggcaccca gacctacatc   660
tgcaacgtga accacaagcc ctccaacacc aaggtggaca agaaggtgga gcctaagagc   720
tgcgacaaga cccacacctg ccctccctgc cccgcccccg agctgctggg cggacccagc   780
gtgttcctgt tccctcccaa gcccaaggac accctgatga tcagccgcac ccccgaggtg   840
acctgcgtgg tggtggacgt gagccacgag gaccccgagg tgaagttcaa ctggtacgtg   900
gacggcgtgg aggtgcacaa cgccaagacc aagcctcggg aggagcagta caactccacc   960
taccgcgtgg tgagcgtgct gaccgtgctg caccaggact ggctgaacgg caaggagtac  1020
aagtgcaagg tgagcaacaa ggccctgccc gctcccatcg agaagaccat cagcaaggcc  1080
aagggccagc cccgggagcc tcaggtgtac accctgcccc cagccgcga cgagctgacc  1140
aagaaccagg tgagcctgac ctgcctggtg aagggcttct accctccga catcgccgtg  1200
gagtgggaga gcaacggcca gcctgagaac aactacaaga ccacccctcc cgtgctggac  1260
agcgacggca gcttcttcct gtacagcaag ctgaccgtgg acaagtcccg gtggcagcag  1320
ggcaacgtgt tcagctgcag cgtgatgcac gaggccctgc acaaccacta cacccagaag  1380
agcctgagcc tgagccccgg aaagtaa                                      1407
```

<210> SEQ ID NO 20
<211> LENGTH: 720
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(720)
<223> OTHER INFORMATION: pCD3_L0041 encoding hGHR106_L41

<400> SEQUENCE: 20

```
atggagaccg acaccctgct gctctgggtg ctgctgctct gggtgcccgg ctccaccgga    60
gatatcgtaa tgactcagtc ccccgatagc ctcgctgtgt cattgggtga acgggcaact   120
attaactgta agtcatcaca agcctccctt aattctagga ccaggaaaaa ctacctggca   180
tggtatcaac agaagccagg acagccacca aagctgctga tctactgggc ttctacaaga   240
gagagtggag tgccagaccg cttctccggc tccgggagcg gcactgattt taccctcact   300
atcagctccc ttcaggcaga ggatgtggcc gtgtactatt gcaagcagag ctacaacctc   360
tacaccttcg gccaggggac taaactggaa attaagcgga ccgtggccgc ccccagcgtg   420
ttcatcttcc ctcccagcga cgagcagctg aagtctggca ccgccagcgt ggtgtgcctg   480
```

```
ctgaacaact tctaccccg cgaggccaag gtgcagtgga aggtggacaa cgccctgcag      540
agcggcaaca gccaggagag cgtgaccgag caggactcca aggacagcac ctacagcctg      600
agcagcaccc tgaccctgag caaggccgac tacgagaagc acaaggtgta cgcctgcgag      660
gtgacccacc agggactgtc tagccccgtg accaagagct caaccgggg cgagtgctaa      720
```

```
<210> SEQ ID NO 21
<211> LENGTH: 720
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(720)
<223> OTHER INFORMATION: pCD3_L0042 encoding hGHR106_L42

<400> SEQUENCE: 21
```

```
atggagaccg acaccctgct gctctgggtg ctgctgctct gggtgcccgg ctccaccgga       60
gatatcgtaa tgactcagtc ccccgatagc ctcgctgtgt cattgggtga acgggcaact      120
attaactgta agtcatcaca aagcctcctt aattctagga ccaggaaaaa ctacctggca      180
tggtatcaac agaagccagg acagtcacca aagctgctga tctactgggc ttctacaaga      240
gagagtggag tgccagaccg cttctccggc tccgggagcg gcactgattt taccctcact      300
atcagctccc ttcaggcaga ggatgtggcc gtgtactatt gcaagcagag ctacaacctc      360
tacaccttcg gccaggggac taaactggaa attaagcgga ccgtggccgc ccccagcgtg      420
ttcatcttcc ctcccagcga cgagcagctg aagtctggca ccgccagcgt ggtgtgcctg      480
ctgaacaact tctaccccg cgaggccaag gtgcagtgga aggtggacaa cgccctgcag      540
agcggcaaca gccaggagag cgtgaccgag caggactcca aggacagcac ctacagcctg      600
agcagcaccc tgaccctgag caaggccgac tacgagaagc acaaggtgta cgcctgcgag      660
gtgacccacc agggactgtc tagccccgtg accaagagct caaccgggg cgagtgctaa      720
```

```
<210> SEQ ID NO 22
<211> LENGTH: 720
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(720)
<223> OTHER INFORMATION: pCD3_L0043 encoding hGHR106_L43

<400> SEQUENCE: 22
```

```
atggagaccg acaccctgct gctctgggtg ctgctgctct gggtgcccgg ctccaccgga       60
gatatcgtaa tgactcagtc ccccgatagc ctcgctgtgt cattgggtga acgggcaact      120
attaactgta agtcatcaca aagcctcctt aattctagga ccaggaaaaa ctacctggca      180
tggtatcaac agaagccagg acagccacca aagctgctga tctactgggc ttctacaaga      240
gagagtggag tgccagaccg cttctccggc tccgggagcg gcactgattt taccctcact      300
atcagctccc ttcaggcaga ggatgtggcc gtgtactatt gcaagcagag ctacaacctc      360
tacaccttcg gcggagggac taaactggaa attaagcgga ccgtggccgc ccccagcgtg      420
ttcatcttcc ctcccagcga cgagcagctg aagtctggca ccgccagcgt ggtgtgcctg      480
ctgaacaact tctaccccg cgaggccaag gtgcagtgga aggtggacaa cgccctgcag      540
agcggcaaca gccaggagag cgtgaccgag caggactcca aggacagcac ctacagcctg      600
```

```
agcagcaccc tgaccctgag caaggccgac tacgagaagc acaaggtgta cgcctgcgag    660
gtgacccacc agggactgtc tagccccgtg accaagagct tcaaccgggg cgagtgctaa    720
```

HUMANIZED FORMS OF MONOCLONAL ANTIBODIES TO HUMAN GNRH RECEPTOR

CROSS-REFERENCE TO RELATED APPLICATIONS

This application claims priority of U.S. Ser. No. 61/676,763 filed 27 Jul. 2012. The contents of these documents are incorporated by reference herein in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 616342000400SeqList.txt, date recorded: Jun. 13, 2013, size: 20,735 bytes).

TECHNICAL FIELD

The invention relates to the field of humanization of GHR106 monoclonal antibody which is of murine origin. GHR106 recognizes specifically the extracellular domains of human GnRH receptor, which is highly expressed on the surface of cancer cells of many human tissue origins. The humanized forms of GHR106 can be utilized for therapeutic applications in human hormone-sensitive cancers as well as in regulating human fertility.

BACKGROUND ART

GHR106 monoclonal antibody was generated in mice immunized against synthetic peptides corresponding to the extracellular domains of human GnRH receptor and was found to behave as a GnRH agonist, but with a much longer half-life than agonists known in the art. GnRH agonists have been used to treat a variety of problems such as ovulation disorders, endometriosis, uterine fibroids, precocious puberty, and some types of cancers.

The murine mAb, GHR106, including the amino acid sequence of its variable regions, is described in PCT publication WO2011/026242, the disclosure of which is incorporated herein by reference, in particular as to uses of antibodies with specificity similar to that of GHR106.

Biochemical and immunological experiments demonstrate that GHR106 has high specificity and affinity to GnRH receptor. In vitro apoptotic and anti-proliferative assays were performed to document that GHR106 reacts with the surface of almost all cancer cells or cancerous tissues in humans. Complement-dependent cytotoxicity can be induced in cancer cells in the presence of GHR106 at concentrations in the range of μg/ml. In vivo growth inhibition by GHR106 of tumor cells implanted in model systems was also demonstrated in nude mouse experiments.

For use of GHR106-based anti-cancer drugs or fertility regulation drugs in humans, it is essential to modify the original murine GHR106 monoclonal antibody into humanized forms.

Disclosure of the Invention

The humanized versions of GHR106 of the invention were shown to have affinities and specificities to GnRH receptor which are comparable or equivalent to those of original murine GHR106.

Figure 6:
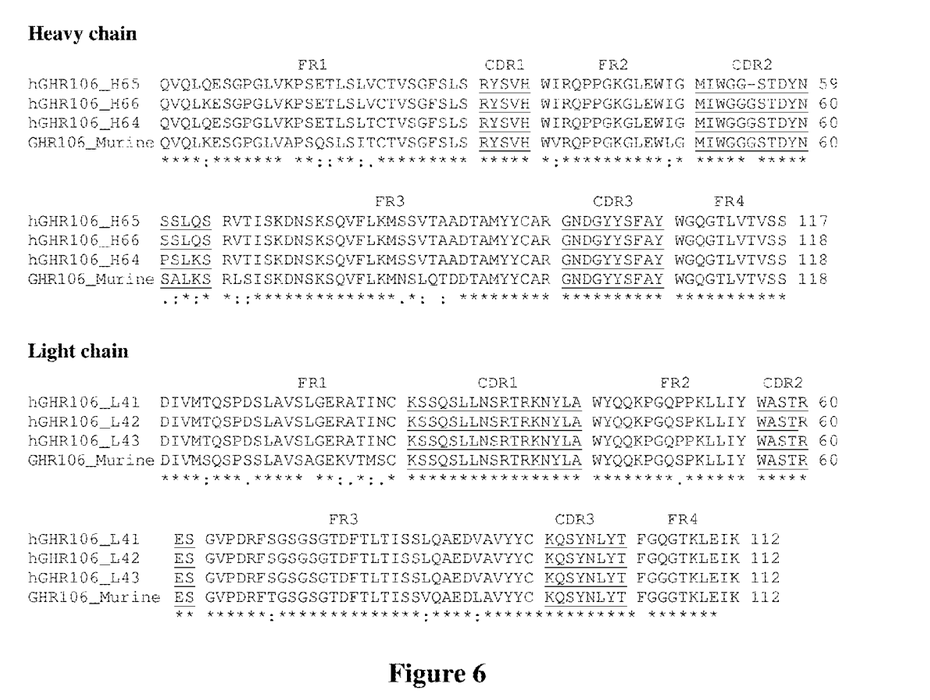
FIG. 6 shows the amino acid sequences of heavy chain and light chain variable regions of humanized forms of GHR106 and of murine GHR106 (SEQ ID NOS:9-16, in order of appearance).

Thus, in one aspect, the invention is directed to humanized antibodies or fragments that bind the epitope present in residues 1-29 in the extracellular domain of the human GnRH receptor, with specificities and affinities substantially equivalent to that of GHR106. In particular, the antibodies or fragments with variable regions shown in FIG. 6 are part of the invention.

For complete antibodies of the invention, it is preferred that the constant region of the heavy chain be IgG and the constant region of the light chain be kappa. However, other Ig forms, including IgM, IgA and IgE for example, are included as well as those embodiments that have lambda constant regions in their light chains.

In still other aspects, the invention is directed to methods to use the antibodies of the invention in the treatment of cancer and controlling reproduction in human subjects.

BRIEF DESCRIPTION OF THE DRAWINGS

FIGS. 7A-C show the nucleotide sequences encoding the variable regions of FIG. 6.

MODES FOR CARRYING OUT THE INVENTION

The humanized antibodies of the invention may be in a variety of forms—including whole antibodies, fragments that are immunoreactive with the epitope present in residues 1-29 in the extracellular domain of the human GnRH receptor, including Fab, Fab', and F(ab')$_2$ fragments as well as recombinantly produced single-chain antibodies. The resulting humanized forms as noted below are of equivalent affinity and specificity to the murine GHR106 and contain substantially similar or identical CDR regions.

The CDR regions of the variable region of both heavy and light chains can be determined by a number of art-known methods, including the numbering system of Kabat which defines, in the light chain, CDR1 as residues 24-34, CDR2 as residues 50-56, CDR3 as residues 89-97 and, in the heavy chain, CDR1 as residues 31-35, CDR2 as residues 50-65 and CDR3 as residues 95-102 (Wu, T. T., and Kabat, E. A., *Exp. Med.* (1970) 132:211-250). CDRs can also be determined according to the system of Clothia which gives slightly different results (Clothia, C., et al., *Nature* (1989) 342:877-883; Al-Laziken, et al., *J. Mol. Biol.* (1997) 273:927-948). Various subsequent authors have suggested some minor modifications. The CDRs as assigned by both Kabat and Clothia systems are included within the scope of the present invention.

Sandwich and/or binding immunoassays were used to demonstrate the substantial equivalence between the humanized forms herein and murine GHR106. Their respective affinity and specificity to the cognate antigen, the epitope present in residues 1-29 in the extracellular domain of the human GnRH receptor, are two important parameters to establish their substantial equivalence.

The previously established sandwich and/or binding immunoassays were used as a tool to demonstrate the substantial equivalence or comparability between the humanized forms and murine GHR106. Their respective affinity and specificity to the cognate antigen in the GnRH receptor establish their substantial equivalence and demonstrates their utility as described for GHR106, but with respect to human subjects.

The following example is offered to illustrate but not to limit the invention.

EXAMPLE 1

Human framework donor selection was made through search of germline followed by rearrangement of the human IgG database using VL and VH sequence with or without CDRs. To obtain human IgG results, normally, each hit is reviewed to eliminate inappropriate donors (such as mouse sequence or humanized sequence, etc.). For VL and VH sequences, the best hits in each group were aligned. Finally, one germline FR donor and one rearranged (mature) FR donor based on sequence similarity and other factors were selected. These factors included CDR length (except for CDR-H3), CDR canonical structure, proline residues at key positions or factors which may affect proper folding of humanized antibody.

The homology modeling was used to obtain template antibody structure by searching the PDB database for the template antibody VL and VH sequences with or without CDR. The following conditions were taken into consideration:
(1) Sequence homology,
(2) CDR length,
(3) CDR canonical structure, and
(4) Model with correct disulfide linkage.

The antigen binding region of the antibody structure model was optimized through the CDR loop database and canonical structure class as well as comparison with the template structure.

CDR Grafting and Back Mutation

Structural modeling was used to identify residues outside of CDR loops that might affect CDR configurations. The following binding or interaction factors were considered: hydrogen bonding, steric hindrance and other interactions of main chain and side chains of CDR residues.

Back mutation was performed to those residues that are predicted significantly to affect CDR loop structure. Other critical residues were also verified including those in (1) the heterodimer interface in FR donors for proper VL and VH interactions, (2) the intra-chain domain interface and (3) the direct interactions to antigen/epitopes in the known structure.

Based on the above considerations, combinations of back mutations were designed to balance the minimal needs of such process. Low immunogenicity to humans and maximal preservation of antigen-binding affinity are obtained.

Preliminary Characterization of Humanized GHR106 Monoclonal Antibodies

After four rounds of humanization designs, several humanized GHR106 monoclonal antibodies were generated, expressed and affinity-purified.

To perform antigen binding assays, cancer cell coated ELISA plates were used to test the affinity of the antibodies. Supernatants containing the various recombinantly produced antibodies from transfected CHO cells were serially diluted and added to ELISA wells for 1 h incubation at 37° C. The plates were subsequently washed with wash buffer, and then incubated with HRP conjugated with goat anti-human IgG antibody for 60 minutes. Afterwards, the plates were washed with wash buffer, and then HRP substrate, TMB, was added to each well for color development. Raw data were collected and analyzed by a microplate reader (POLARstar Omega from BMG Labtech).

All antibodies were produced with human IgG heavy chain constant regions and light chain kappa constant regions.

First Round Humanization

The first round humanization design generated three heavy chains (H41 through H43) and three light chains (L41 through L43). Each designed sequence was gene synthesized and cloned to make both full-length heavy and light chains. Each DNA was sequence confirmed. A 4×4 matrix (Table 1) was designed to generate 16 recombinant antibodies (including the parental control antibody composed of H40 and L40). DNA for each antibody pair was transfected into adherent CHO cells to produce recombinant antibody.

TABLE 1

Antibody pair matrix for the first round 16 recombinant antibodies

|     | H40 | H41 | H42 | H43 |
|-----|-----|-----|-----|-----|
| L40 | #1  | #5  | #9  | #13 |
| L41 | #2  | #6  | #10 | #14 |
| L42 | #3  | #7  | #11 | #15 |
| L43 | #4  | #8  | #12 | #16 |

Five days after transfection, the media from CHO cells were collected and the IgG levels in the conditioned media were measured by an anti-human IgG/Fc ELISA (LakePharma Product catalog number 2001002). Although there is variation in the production levels, each antibody pair was produced and secreted, as shown in Table 2 below.

TABLE 2

Human IgG levels (ng/mL) in the conditioned media for each antibody pair.

|     | H40  | H41  | H42  | H43  |
|-----|------|------|------|------|
| L40 | 4777 | 3011 | 2178 | 2130 |
| L41 | 4024 | 6026 | 2488 | 1726 |
| L42 | 4718 | 2341 | 1829 | 2401 |
| L43 | 4854 | 3035 | 2886 | 9256 |

Figure 1:
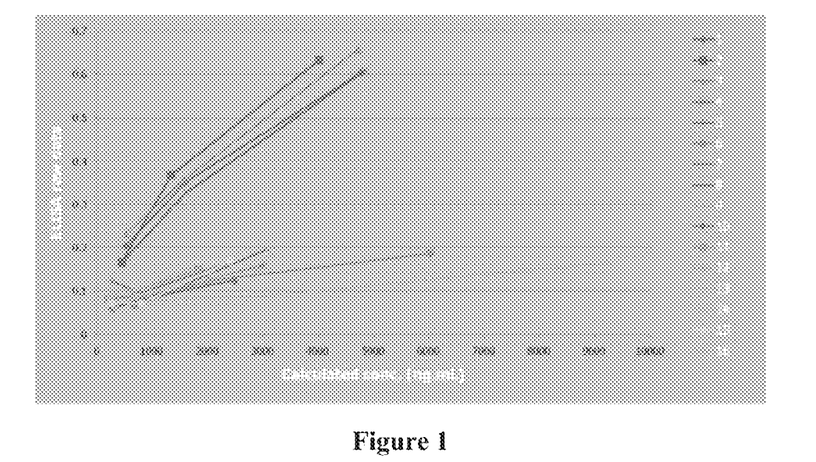
FIG. 1 shows antigen binding affinity of humanized antibodies after a first round of humanization as described herein.

FIG. 1 shows the results of the antigen binding assay described above and dose response after the first round humanization. All antibodies with humanized light chains with parental H40 produced antibodies with significant binding affinity. None of the antibodies with three humanized heavy chains showed significant binding affinity.

Second Round Humanization

Figure 2:
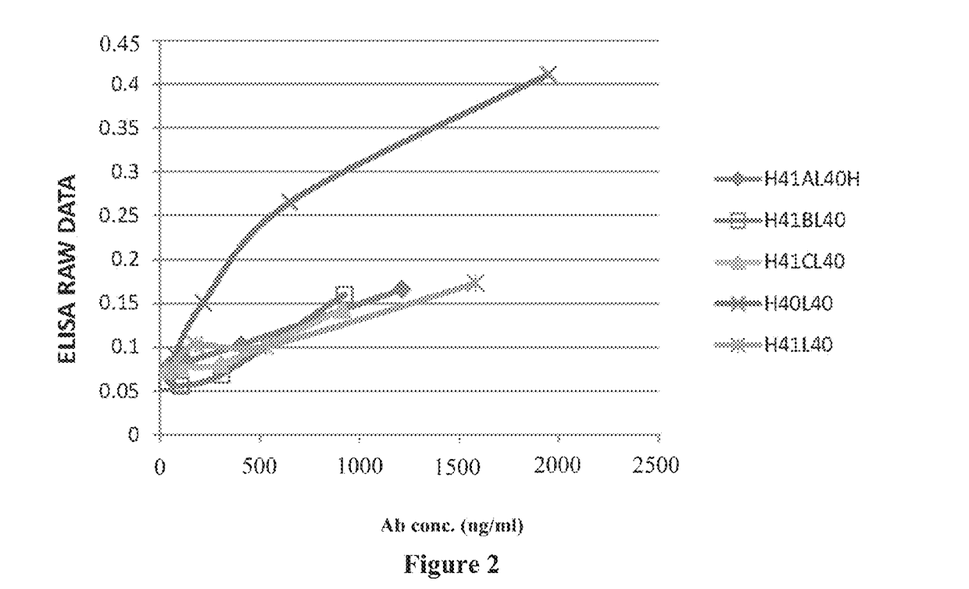
FIG. 2 shows antigen binding affinity of humanized antibodies after a second round.

Three more humanized heavy chains (H41A, H41B and H41C) were designed. Three more antibodies H41A-L40, H41B-L40 and H41C-L40 were produced and assayed. FIG. 2 shows the antigen binding assay and dose response after the second round humanization. None of the second round three humanized heavy chains showed significant binding affinity.

Third Round Humanization

Figure 3:
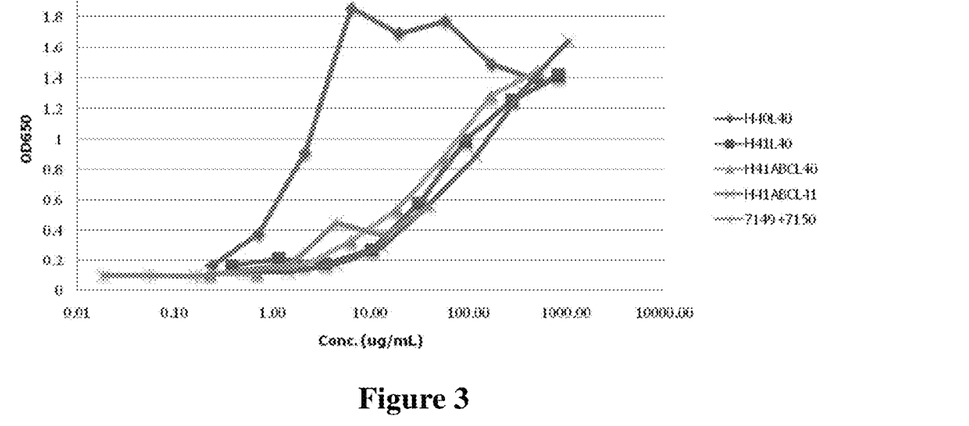
FIG. 3 shows antigen binding affinity of humanized antibodies after a third round.

Humanized heavy chain H41ABC therefore was made and two more antibodies (H41ABC-L40, H41ABC-L41) were produced and assayed. Antibody 7149+7150 was included in the assay as the negative control. FIG. 3 shows the antigen binding assay and dose response after the third round humanization. Humanized heavy chain H41ABC did not show significant binding affinity.

Fourth Round Humanization

The fourth round humanization design started from scratch and generated three new heavy chains (H64 through H66). The binding assays had shown that humanized light chain L42 demonstrated strong binding to the antigen when combined with parental heavy chain H40. Therefore, a set of five antibodies (Table 3) were designed to be tested (including the parental control antibody and a negative control antibody 7149+7150).

Figure 4:
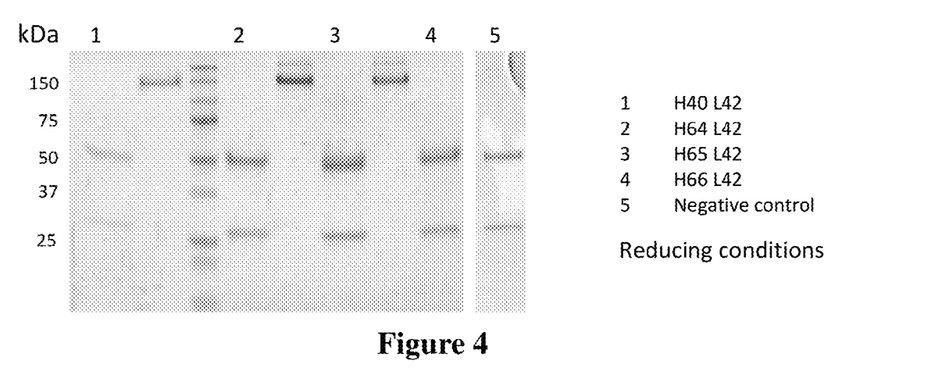
FIG. 4 shows SDS-PAGE image of purified recombinant antibodies.

Plasmids for the antibodies, H64-L42, H65-L42, H66-L42, H40-L42 and 7149+7150 were transfected to 100 mL suspension CHO cells using chemically defined media and in the absence of serum to make the antibodies. Seven days after transfection, the conditioned media were collected and clarified. Whole antibodies in the conditioned media were purified using Protein A beads (MabSelect SuRe™, GE Healthcare). The purified samples were resolved by SDS-PAGE (FIG. 4), and antibody concentration was quantified by UV spectrophotometer (Table 3).

TABLE 3

Composition and production yield of recombinant antibodies

|   | Heavy chain | Light chain | UV 280 (mg/mL) |
|---|---|---|---|
| 1 | H64 | L42 | 0.37 |
| 2 | H65 | L42 | 0.26 |
| 3 | H66 | L42 | 0.41 |
| 4 | H40 | L42 | 0.43 |
| 5 | Negative control | Negative control | 0.02 |

Figure 5:
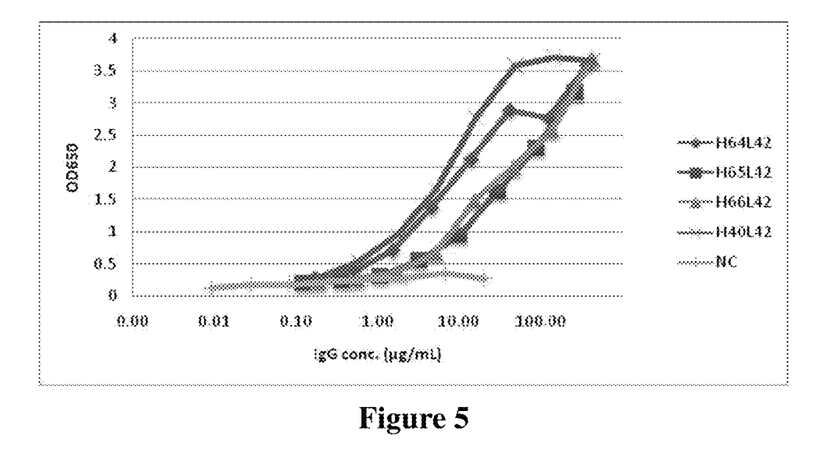
FIG. 5 shows antigen binding affinity of humanized antibodies after a fourth round.

The antigen binding dose response (Table 4) curves are shown in FIG. 5, and the binding titer was determined by GraphPad Prism software, as reported in Table 5.

TABLE 4

Raw antigen binding ELISA data

| 1 | 2 | 3 | 4 | 5 | 6 | 7 |
|---|---|---|---|---|---|---|
| 3.597 | 3.164 | 3.683 | 3.663 | 3.584 | 2.216 | 0.271 |
| 2.766 | 2.298 | 2.575 | 3.712 | 2.668 | 0.934 | 0.359 |
| 2.88 | 1.625 | 1.998 | 3.585 | 2.257 | 0.671 | 0.275 |
| 2.129 | 0.938 | 1.477 | 2.778 | 1.455 | 0.474 | 0.257 |
| 1.373 | 0.552 | 0.665 | 1.663 | 0.826 | 0.247 | 0.227 |

TABLE 4-continued

Raw antigen binding ELISA data

| 1 | 2 | 3 | 4 | 5 | 6 | 7 |
|---|---|---|---|---|---|---|
| 0.712 | 0.31 | 0.373 | 0.955 | 0.357 | 0.242 | 0.178 |
| 0.396 | 0.237 | 0.246 | 0.531 | 0.328 | 0.201 | 0.175 |
| 0.281 | 0.207 | 0.218 | 0.291 | 0.234 | 0.181 | 0.129 |

TABLE 5

Binding potency of purified antibodies

|   | Antibody | Binding Potency (ng/ml) |
|---|---|---|
| 1 | H64L42 | 13 |
| 2 | H65L42 | 50 |
| 3 | H66L42 | 43 |
| 4 | H40L42 | 7 |
| 5 | NC | 326 |

Figure 7C:
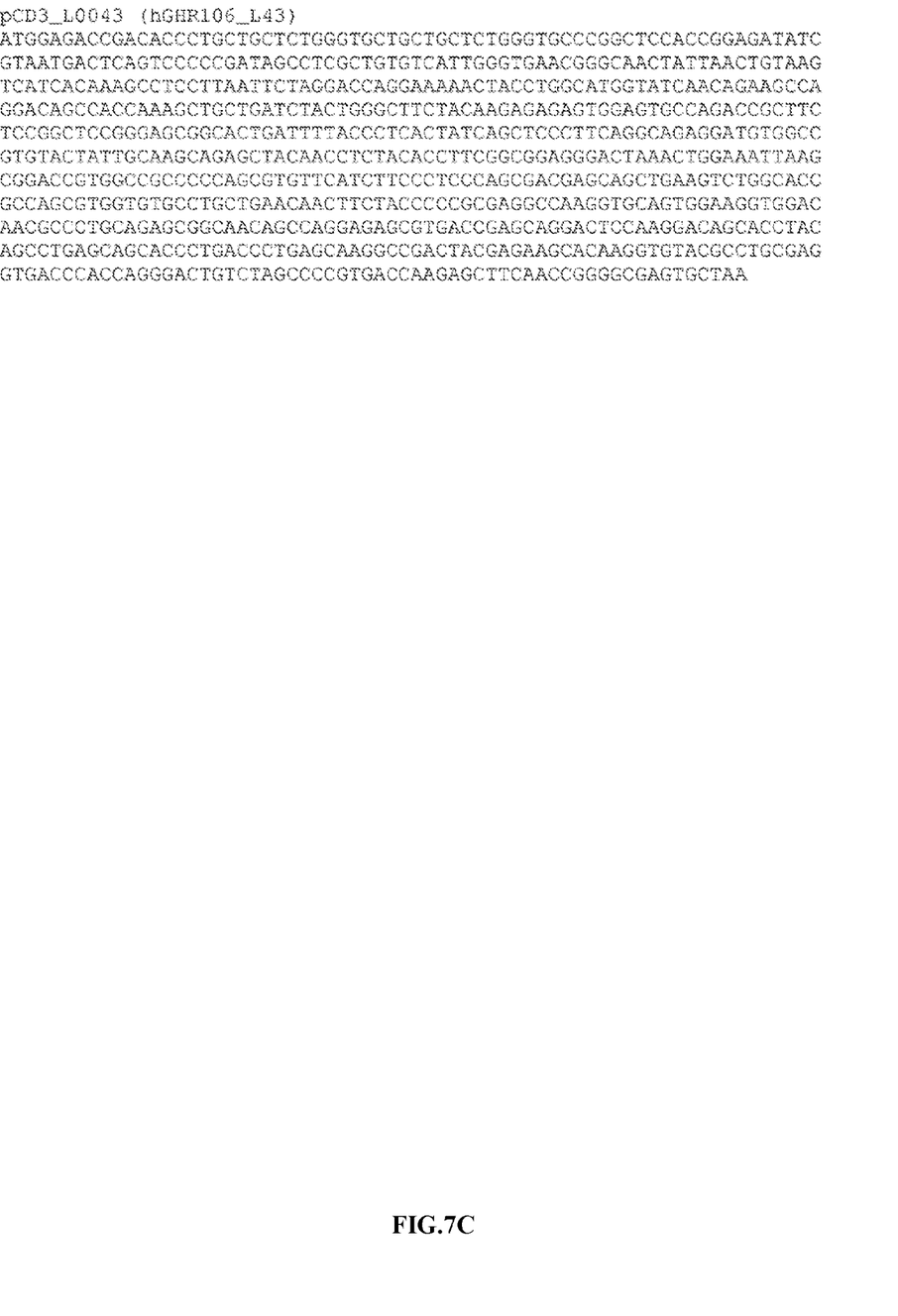

Thus, humanization of GHR106 has been successfully completed after four rounds of humanization. All three humanized light chains showed good potency, comparable to the parental light chain. L42 was selected for later humanized antibody assays. In total, 10 humanized heavy chains of four rounds have been made. H64 from the fourth round showed good potency, comparable to the parental heavy chain H40. In summary, H64L42 appears to be the best humanized pair with comparable potency as the parental antibody. FIG. 6 shows the comparison of amino acid sequences of heavy chain and light chain of humanized forms of GHR106 with those of murine GHR106. FIG. 7 shows their encoding nucleic acid sequences.

Thus, various antibodies and fragments of the invention are antibodies Ab1-Ab9 shown in Table 6

TABLE 6

|   | L41 | L42 | L43 |
|---|---|---|---|
| H64 | Ab1 | Ab2 | Ab3 |
| H65 | Ab4 | Ab5 | Ab6 |
| H66 | Ab7 | Ab8 | Ab9 |

The invention claimed is:

1. A humanized monoclonal antibody (mAb) or an antigen-binding fragment thereof that reacts specifically with an epitope present in amino acid residues 1-29 of the extracellular domain of the human GnRH receptor,
    wherein the heavy chain comprises the variable region of H64 encoded by SEQ ID NO:17 and the light chain comprises the variable region of L41 encoded by SEQ ID NO:20, or
    wherein the heavy chain comprises the variable region of H64 encoded by SEQ ID NO:17 and the light chain comprises the variable region of L42 encoded by SEQ ID NO:21, or
    wherein the heavy chain comprises the variable region of H64 encoded by SEQ ID NO:17 and the light chain comprises the variable region of L43 encoded by SEQ ID NO:22, or
    wherein the heavy chain comprises the variable region of H65 encoded by SEQ ID NO:18 and the light chain comprises the variable region of L41 encoded by SEQ ID NO:20, or
    wherein the heavy chain comprises the variable region of H65 encoded by SEQ ID NO:18 and the light chain comprises the variable region of L42 encoded by SEQ ID NO:21, or
    wherein the heavy chain comprises the variable region of H65 encoded by SEQ ID NO:18 and the light chain comprises the variable region of L43 encoded by SEQ ID NO:22, or
    wherein the heavy chain comprises the variable region of H66 encoded by SEQ ID NO:19 and the light chain comprises the variable region of L41 encoded by SEQ ID NO:20, or
    wherein the heavy chain comprises the variable region of H66 encoded by SEQ ID NO:19 and the light chain comprises the variable region of L42 encoded by SEQ ID NO:21, or
    wherein the heavy chain comprises the variable region of H66 encoded by SEQ ID NO:19 and the light chain comprises the variable region of L43 encoded by SEQ ID NO:22.

2. The mAb of claim 1 that is a complete antibody.

3. The fragment of claim 1 which is an F(ab')$_2$, Fab, Fv, or scFv fragment.

4. The mAb or fragment of claim 1, coupled to a detectable marker or to a therapeutic agent.

5. A pharmaceutical composition comprising the antibody or fragment of claim 1 and a pharmaceutically acceptable excipient.

6. The pharmaceutical composition of claim 5 further comprising an additional therapeutic agent.

7. The mAb or fragment of claim 1 wherein the heavy chain comprises the variable region of H64 encoded by SEQ ID NO:17 and the light chain comprises the variable region of L41 encoded by SEQ ID NO:20.

8. The mAb or fragment of claim 1 wherein the heavy chain comprises the variable region of H64 encoded by SEQ ID NO:17 and the light chain comprises the variable region of L42 encoded by SEQ ID NO:21.

9. The mAb or fragment of claim 1 wherein the heavy chain comprises the variable region of H64 encoded by SEQ ID NO:17 and the light chain comprises the variable region of L43 encoded by SEQ ID NO:22.

10. The mAb or fragment of claim 1 wherein the heavy chain comprises the variable region of H65 encoded by SEQ ID NO:18 and the light chain comprises the variable region of L41 encoded by SEQ ID NO:20.

11. The mAb or fragment of claim 1 wherein the heavy chain comprises the variable region of H65 encoded by SEQ ID NO:18 and the light chain comprises the variable region of L42 encoded by SEQ ID NO:21.

12. The mAb or fragment of claim 1 wherein the heavy chain comprises the variable region of H65 encoded by SEQ ID NO:18 and the light chain comprises the variable region of L43 encoded by SEQ ID NO:22.

13. The mAb or fragment of claim 1 wherein the heavy chain comprises the variable region of H66 encoded by SEQ ID NO:19 and the light chain comprises the variable region of L41 encoded by SEQ ID NO:20.

14. The mAb or fragment of claim 1 wherein the heavy chain comprises the variable region of H66 encoded by SEQ ID NO:19 and the light chain comprises the variable region of L42 encoded by SEQ ID NO:21.

15. The mAb or fragment of claim 1 wherein the heavy chain comprises the variable region of H66 encoded by SEQ ID NO:19 and the light chain comprises the variable region of L43 encoded by SEQ ID NO:22.

* * * * *